(12) United States Patent
Dagiral et al.

(10) Patent No.: US 9,366,604 B2
(45) Date of Patent: Jun. 14, 2016

(54) CYTOLOGICAL OR HISTOLOGICAL BINDING COMPOSITION AND STAINING METHODS

(75) Inventors: Rodolphe Louis Guy Dagiral, Villenave D'Ornon (FR); Florian Montiel, Pomerol (FR)

(73) Assignee: R.A.L. DIAGNOSTICS, Martillac (FR)

( * ) Notice: Subject to any disclaimer, the term of this patent is extended or adjusted under 35 U.S.C. 154(b) by 0 days.

(21) Appl. No.: 13/384,845

(22) PCT Filed: Jul. 21, 2010

(86) PCT No.: PCT/FR2010/051540
§ 371 (c)(1),
(2), (4) Date: Jan. 19, 2012

(87) PCT Pub. No.: WO2011/010064
PCT Pub. Date: Jan. 27, 2011

(65) Prior Publication Data
US 2012/0122151 A1 May 17, 2012

(30) Foreign Application Priority Data
Jul. 22, 2009 (FR) ...................................... 09 55127

(51) Int. Cl.
*G01N 1/30* (2006.01)
(52) U.S. Cl.
CPC ........................................ *G01N 1/30* (2013.01)
(58) Field of Classification Search
None
See application file for complete search history.

(56) References Cited

FOREIGN PATENT DOCUMENTS

| FR | 2 854 239 | A1 | 10/2004 |
|----|-----------|----|---------|
| WO | 92/19951  | A1 | 11/1992 |
| WO | 94/07532  | A1 | 4/1994  |
| WO | 2008/043963 | A1 | 4/2008 |

OTHER PUBLICATIONS

Greenhalf et al., Role of mitochondria and C-terminal membrane anchor of Bcl-2 in Bax induced growth arrest and mortality in *Saccharomyces cerevisiae*, FEBS Letters, 1996, pp. 169-175.*
Toxic, Merriam-Webster dictionary, accessed May 20, 2014, http://www.merriam-webster.com/dictionary/toxic.*
Ethanol, MSDS, NEOGEN Corporation, accessed May 21, 2014, http://www.neogen.com/FoodSafety/pdf/msds/8058_59_MSDS.pdf.*
Ethylene Glycol, EPA, Technology Transfer Network—Air Toxics Web Site, accessed on May 21, 2014, http://www.epa.gov/ttnatw01/hlthef/ethy-gly.html.*
Sigma Aldrich Pictograph, accessed Feb. 9, 2015, http://www.sigmaaldrich.com/help-welcome/hazard-and-precautionary-statements.html#pictogram.*
Fishersci ethanol, MSDS, Fisher Scientific, accessed Feb. 9, 2015, http://fscimage.fishersci.com/msds/89308.htm.*
OSHA Occupational Chemical Database Ethylene Glycol, accessed Feb. 9, 2015, https://www.osha.gov/chemicaldata/chemResult.html?recNo=63.*
International Search Report, dated Nov. 9, 2010, from corresponding PCT application.

* cited by examiner

*Primary Examiner* — Louise W Humphrey
*Assistant Examiner* — Christopher Keller
(74) *Attorney, Agent, or Firm* — Young & Thompson (57) ABSTRACT

A histological and cytological fixing composition, includes at least alcohol, ethylene glycol, dimethyl sulfoxide, water, and sodium chloride. Also, process for preparing this fixer, as well as to its use in particular in processes for staining cells or cellular structures are described.

15 Claims, 5 Drawing Sheets

CYTOLOGICAL OR HISTOLOGICAL BINDING COMPOSITION AND STAINING METHODS

This invention relates to a composition for fixing tissues, cells or cellular components on plates for the purpose of the staining and analysis thereof.

The invention also relates to a process for preparation of this fixer and its use in histology or cytology. A particular use of this invention is a process for staining tissues, cells or cellular components, in particular for blood and marrow, using this fixer.

To identify tissues, cells or parts of cells, cellular staining techniques combined with microscopic observation or with image analysis systems are used.

These staining methods are necessary in numerous areas of biology, both in basic research as well as in medical or veterinary analysis for tissue diagnostics or cytodiagnostics.

In hematology in particular, the staining known under the name of MGG, May-Grünwald Giemsa, has been used for a great many years. The staining process consists in:
- Fixing the cells to be stained on a plate with a May-Grünwald solution that consists of methylene blue-eosin that is dissolved in methanol,
- Bringing the plate into contact with a buffered solution,
- Then bringing it into contact with a Giemsa solution that consists of azure blue II-eosin dissolved in methanol with glycerin,
- And finally in rinsing it and drying it.

Stainings that are known to all practitioners who make a standard of this technique are then obtained and make it possible to establish reliable comparisons.

Nevertheless, the MGG staining exhibits numerous drawbacks. In particular, it uses toxic and volatile solvents. In addition, the presence of glycerin also produces drawbacks because it makes it more difficult to rinse the plates and can cause clogging of the filters during filtration.

In addition, to produce good staining, it is important that the stain be stable and that deposits of stain do not persist after the plate is rinsed. However, such deposits may appear with the MGG. These deposits disturb the operation of the automatic staining devices and cell identification systems and hamper the distinguishing of different cell elements and the identification of healthy cells versus sick cells in the case of cytodiagnostics.

So as to avoid these drawbacks, attempts have been made to replace the MGG by other staining processes.

However, a majority of the processes developed for replacing the MGG do not make it possible either to preserve its essential reproducibility for analysis or to obtain comparable results.

In addition, like the MGG, they use methanol, whether it is to produce the stain itself or the cell fixing solution. As a matter of fact, methanol has particular physical properties that make it possible for it to fix the cells properly.

However, the methanol is a toxic and volatile product whose use it is desirable to limit because it may prove dangerous to the practitioner.

Solutions have been proposed by replacing methanol by ethanol, but ethanol by itself does not provide satisfactory results, in particular when it is used for fixing.

Other solutions consist in using picric acid, formaldehyde, glutaraldehyde or else osmic acid as an agent for fixing cellular structures.

However, while the results that are obtained can be of high quality, the presence of toxic products involves risks for the individuals who have occasion to handle them.

Furthermore, with the development of image analysis systems, it is necessary to use automatic staining systems so as to ensure that the staining stages always proceed identically. However, with the current reagents and fixing products, these machines undergo heavy maintenance, because they cause a rapid clogging of circuits and reservoirs.

Finally, it is known that, in a historic way, depending on the countries in question, the staining reagents can be different for the same field of biology. This is reflected by different tints and a more or less notable display of a certain type of cellular element. In hematology, a distinction is conventionally made between stains that involve a combination of staining reagents (such as the MGG stains used in the "European culture" countries) and stains that involve a single staining reagent (such as the stains of Wright and Leishman, used in the "English or Asian culture" countries). However, the fixing solutions that are currently used are specific to a given staining process, and it is not possible to use the same fixer for two different processes.

There is therefore still a need for products designed for staining tissues, cells or cellular components that are non-toxic, stable, economical, and easy-to-use and that make it possible to obtain results that are reproducible and suitable for automatic staining devices. In particular, there is still a need for a product for fixing tissues, cells or cellular elements on plates for the purpose of being studied under a microscope, which meets these requirements and which adapts to various staining processes.

This is the purpose of this invention in proposing to use a histological or cytological fixing composition that eliminates the drawbacks of the prior art, particularly suited to the field of hematology.

For this purpose, the object of the invention is the use of a composition that comprises at least:
- An alcohol,
- Dimethyl sulfoxide,
- Ethylene glycol,
- Water, and
- Sodium chloride, for fixing tissues, cells or cellular components on a plate for the purpose of the staining and analysis thereof under a microscope or by an image analysis system.

The purpose of the invention is also the histological or cytological fixing composition, or fixer, that is used.

Advantageously, such a fixing composition does not contain toxic product. It makes it possible to efficiently preserve the cells for the purpose of their staining so as to obtain reproducible and stable results that can be easily analyzed under a microscope or by image analysis systems.

The invention also relates to a process for preparation of this composition.

Preferably, the fixing composition also comprises at least one blue stain and one red stain and can be used simultaneously both for fixing and staining the cells.

Finally, the object of the invention is also a process for staining cells or cellular elements, suitable in particular for blood and marrow, using the fixing composition.

Advantageously, the process according to the invention makes it possible to obtain reproducible results of a very good quality. In addition, it is economical, fast, reliable, easy to use, and requires only a low stain content.

The invention is now described in detail relative to the accompanying figures in which.

The object of the invention is the use for carrying out the fixing of tissues and/or cells and/or cellular structures on a plate for the purpose of the staining and analysis thereof under a microscope or using an image analysis system of a composition that comprises at least one alcohol, dimethyl sulfoxide, ethylene glycol, water and sodium chloride.

Preferably, the composition is used for fixing cells and/or cellular structures of blood or marrow.

Advantageously, the composition can also contain one or more stains and be used for simultaneously carrying out the fixing and the staining of tissues and/or cells and/or cellular structures.

The invention also relates to a particular composition of histological or cytological fixing, also called a fixer.

In terms of this invention, a fixing composition or fixer is defined as a reagent that makes it possible to stop the phenomena of cell and tissue autolysis so that they preserve an appearance that is as close as possible to that which they had in the live state. Such a reagent therefore makes it possible to preserve the morphology and to immobilize the cells and tissues for the purpose of producing microscopic preparations that can be preserved. It should also make it possible to implement additional treatments, such as stainings, histochemical or immunological reactions, so as to demonstrate certain structural, functional or genetic aspects of the cells and tissues.

The composition comprises at least one alcohol, dimethyl sulfoxide, ethylene glycol, water and sodium chloride.

The alcohol can be selected from among all the non-toxic alcohols. Preferably, alcohol is ethanol or isopropanol.

It may also involve a mixture of alcohols.

According to a particularly suitable embodiment, the alcohol is ethanol. The water can be demineralized water or deionized water.

So as to obtain a better effectiveness of the composition, the water and the sodium chloride should be present in particular proportions. Also, according to one particularly suitable embodiment, sodium chloride is present between 0.1 and 0.5% by mass of the total of the composition, and water is present between 2 and 12%, preferably between 2.6 and 8.0%, by mass of the total of the composition. Even more preferably, sodium chloride is present between 0.2 and 0.3%, and water is present between 3 and 6%. Likewise, alcohol is present between 40 and 60% by mass of the total of the composition, and ethylene glycol is present between 0.1 and 1% by mass of the total of the composition. Even more preferably, alcohol is present between 50 and 60%, and ethylene glycol is present between 0.1 and 0.5%.

In addition, particularly advantageous results are obtained when the DMSO is present between 30 and 40% by mass of the total of the composition.

By comparing the different FIGS. 3a to 6c, it is noted that the presence of each of the components—alcohol, ethylene glycol, dimethyl sulfoxide, sodium chloride and water—is significant. It is the mixture of these particular components that makes it possible for the composition to be able to fix the cells, which can then be easily stained and analyzed.

In FIGS. 3a to 6c, the cells are fixed with compositions that comprise all or part of the components of the composition according to the invention, and then stained by a quick staining technique like the one used in the RAL 555 (RAL®) kit: the fixed plate is immersed in a first red stain for 5 seconds and then in a blue stain for 5 seconds, and finally, the plate is rinsed and dried. The results that are obtained are better when alcohol, ethylene glycol, dimethyl sulfoxide, sodium chloride and water are present in the fixing composition.

The composition according to the invention can be obtained by a manufacturing process that comprises at least the implementation of the following stages:

Mixing alcohol and ethylene glycol in such a way as to obtain a solution 1,

Dissolving sodium chloride in water in such a way as to obtain a solution 2,

Adding the solution 2 into the solution 1, while being stirred, and then dimethyl sulfoxide, and Filtration.

According to a variant, the fixing composition according to the invention also comprises at least one blue stain and at least one red stain.

The blue stain can be selected from among methylene blue and/or azure blue I and/or a blue stain that belongs to the group of thiazines.

The red stain can be selected from among eosin and/or erythrosine.

Preferably, the blue and red stain(s) are dissolved in dimethyl sulfoxide.

According to one particularly suitable embodiment, the composition according to the invention comprises:

Dimethyl sulfoxide,
An alcohol, for example ethanol or isopropanol, or a mixture of alcohols,
Ethylene glycol,
Water,
Sodium chloride,
Methylene blue-eosin,
Azure blue I-eosin,
Methylene blue,
Methylene azure blue I, and
A compound of the group of thiazines.

In particular, the composition according to the invention can comprise:
Approximately 32% (by volume) of DMSO,
Approximately 63% (by volume) of alcohol,
Approximately 0.1% (by volume) of ethylene glycol,
Approximately 4.9% (by volume) of water,
Approximately 20% (by weight of dry material) of methylene blue-eosin,
Approximately 20% (by weight of dry material) of azure blue I-eosin,
Approximately 8% (by weight of dry material) of methylene blue,
Approximately 8% (by weight of dry material) of methylene azure blue I,
Approximately 4% (by weight of dry material) of a compound of the group of thiazines, and
Approximately 40% (by weight of dry material) of sodium chloride.

Advantageously, such a composition makes it possible simultaneously to carry out the staining and fixing of tissues, cells, or cellular components.

It can be obtained by a manufacturing process that comprises at least the implementation of the following stages:
Preparing a solution 4 that comprises at least dimethyl sulfoxide, a blue stain, and a red stain,
Mixing an alcohol and ethylene glycol in such a way as to obtain a solution 1,
Dissolving sodium chloride in water in such a way as to obtain a solution 2,
Adding the solution 2 into the solution 1, while being stirred, in such a way as to obtain a solution 3,
Adding the solution 3, while being stirred, into the solution 4, and
Filtration.

The stains of solution 4 are dissolved in DMSO.
Preferably, the alcohol is ethanol.
Advantageously, the fixer according to the invention lacks toxic products while allowing a good fixing of tissues, cells and cellular structures. It is particularly suitable for fixing blood and medullary smears.

According to another advantage, the fixing composition can be used in different ways and applied to different staining processes, both those involving a combination of staining reagents and those involving a single staining reagent.

Nevertheless, the particular staining processes that implement this fixer are the object of the invention. They involve processes for staining cells or cellular structures, in particular for blood and marrow.

These processes comprise at least one stage that consists in bringing into contact the preparation to be stained with a fixing composition that is the object of the invention.

According to a first variant, the staining process comprises at least the following stages:
Bringing into contact a preparation to be stained, for example a plate that bears blood or medullary smears to be analyzed, with a fixing composition according to the invention, for preferably between 5 and 10 minutes;
Bringing into contact the preparation that is fixed with a buffer solution at a pH of between 6.5 and 7, for preferably between 3 and 8 minutes, in such a way as to trigger and control the staining process that is prepared by the fixer according to the invention; it may be advantageous in this stage not to eliminate the entire fixer when it passes into the buffer solution,
Bringing into contact, optionally by stirring gently, the preparation with a rinsing solution, for preferably between 5 and 20 seconds, whose functions are to stop the staining by eliminating the excess stains and to refine the staining of cellular structures.

This process corresponds to a "Wright/Leishman-staining"-type staining.

According to a second variant, the staining process comprises at least the following stages:
Bringing a preparation to be stained into contact with a fixing composition according to the invention, for preferably between 5 and 8 minutes,
Bringing the fixed preparation into contact with a buffer solution at a pH of between 6.8 and 7.2, for preferably between 2 and 3 minutes, in such a way as to trigger and control the staining process prepared by the fixer according to the invention,
Bringing the preparation into contact, optionally by stirring gently, with an additional staining reagent, for preferably between 1 and 3 minutes, which acts in a buffered medium and makes it possible to perfect the staining for certain conditions of use,
Bringing the preparation into contact with a rinsing solution, for preferably between 5 and 20 seconds.

This process corresponds to a May-Grünwald-Giemsa-staining"-type staining.

The buffer that is used for implementing processes according to the invention can consist of water, disodium phosphate, monopotassium phosphate, an anti-microbial agent, and a non-ionic surfactant.

The additional staining reagent may consist of methylene blue, methylene azure blue I, and a compound from the group of thiazines dissolved in DMSO, and disodium phosphate and monopotassium phosphate dissolved in water.

The rinsing liquid may consist of disodium phosphate, monopotassium phosphate, an anti-microbial agent, and isopropanol dissolved in water.

After air-drying, the plates are ready to be observed directly under a microscope or by an image analysis system.

Advantageously, with the products used, in particular with the fixer according to the invention, it is possible to ensure a standardization of stains and to obtain a reproducibility of colors. They are linked to the composition of products, in particular of the fixer, but also because ready-to-use products are involved. Actually, the use of such products prevents introducing a human factor into the preparation of the solutions, in particular by eliminating the stages of dilution and use of additional products of variable quality that degrade the quality and the reproducibility of stains.

This reproducibility constitutes a stable reference on which the image analysis systems can be supported. These systems, responsible for identifying and classifying the different cellular types by spotting the potential anomalies that are possible signs of the presence of a pathology, can only be used if the results that are obtained are reproducible.

In addition, the fixer and the reagents that are used according to the invention can be used in automatic staining devices, because their use limits the deposits, thus considerably reducing the cost of use of these machines.

Figure 1A:
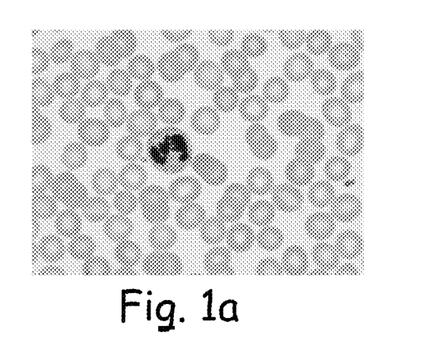
FIG. 1a shows a blood smear after MGG staining.
Figure 1B:
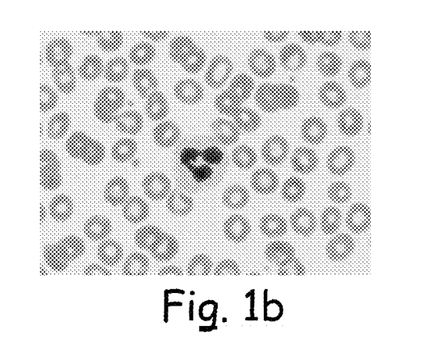
FIG. 1b shows a blood smear after MGG staining with poor fixing.
Figure 1C:
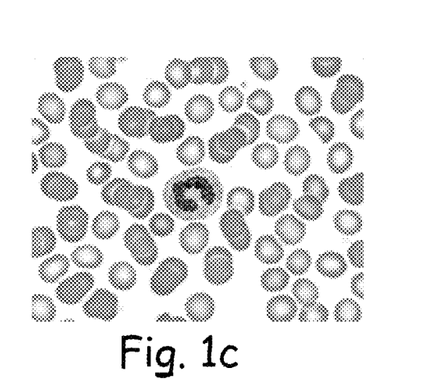
FIG. 1c shows a blood smear after Wright staining.
Figure 1D:
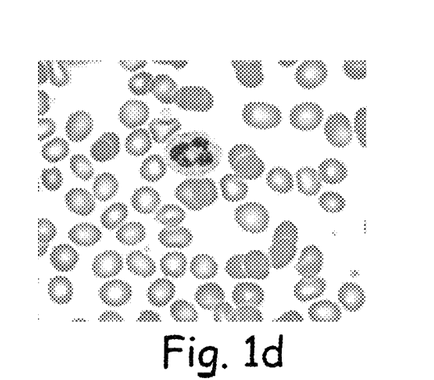
FIG. 1d shows a blood smear after Leishman staining.
Figure 2A:
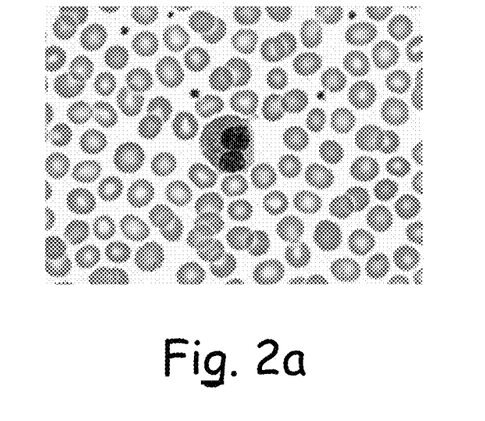
FIG. 2a shows a blood smear after fixing and staining by the composition according to the invention, by the implementation of an MGG-staining-type staining process.
Figure 2B:
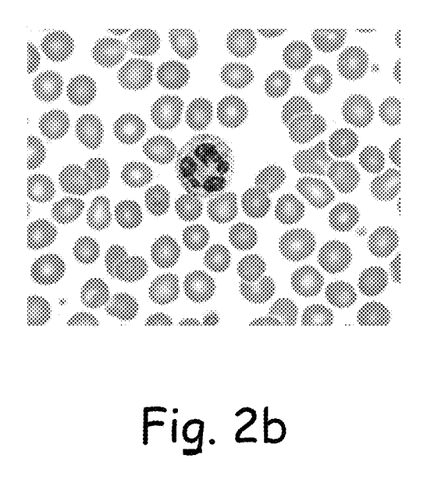
FIG. 2b shows a blood smear after fixing and staining by the composition according to the invention, by the implementation of a Wright/Leishman-staining-type staining process.
Figure 3A:
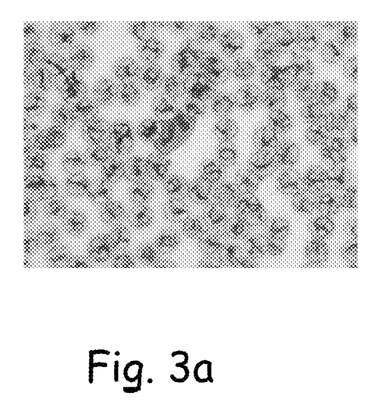
FIG. 3a shows a blood smear after a quick staining with a process that comprises a preliminary fixing stage for 1 minute with ethanol at 70°+2% ethylene glycol.
Figure 3B:
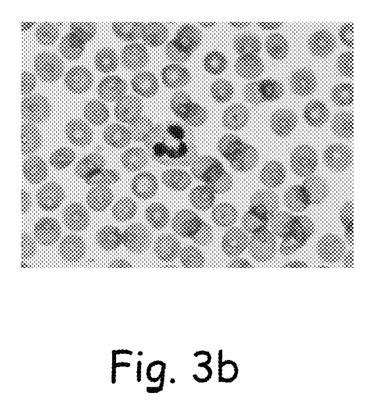
FIG. 3b shows a blood smear after a quick staining with a process that comprises a preliminary fixing stage for 1 minute with ethanol at 99.9°+2% ethylene glycol.
Figure 3C:
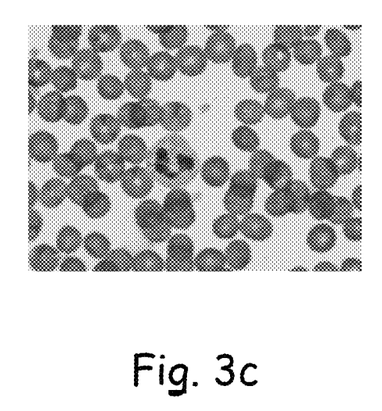
FIG. 3c shows a blood smear after a quick staining with a process that comprises a preliminary fixing stage for 5 minutes with ethanol at 99.9°+2% ethylene glycol.
Figure 4:
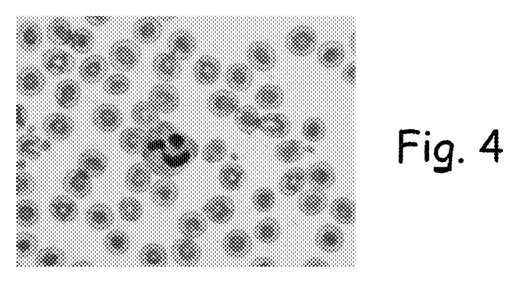
FIG. 4 shows a blood smear after a quick staining with a process that comprises a preliminary fixing stage for 5 minutes with ethanol at 99.9°+2% ethylene glycol+dimethyl sulfoxide.
Figure 5A:
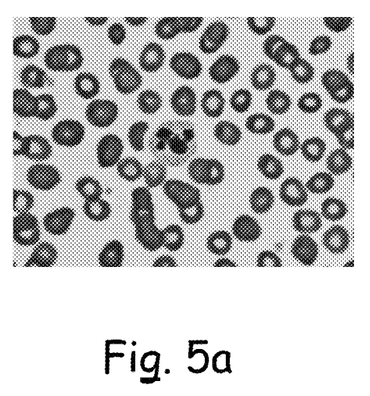
FIG. 5a shows a blood smear after a quick staining with a process that comprises a preliminary fixing stage for 5 minutes with ethanol at 99.9°+2% ethylene glycol+dimethyl sulfoxide+5 ml of water.
Figure 5B:
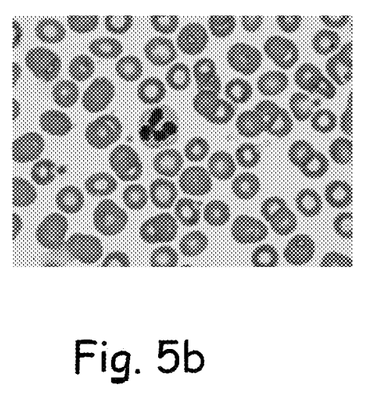
FIG. 5b shows a blood smear after a quick staining with a process that comprises a preliminary fixing stage for 5 minutes with ethanol at 99.9°+2% ethylene glycol+dimethyl sulfoxide+10 ml of water.
Figure 5C:
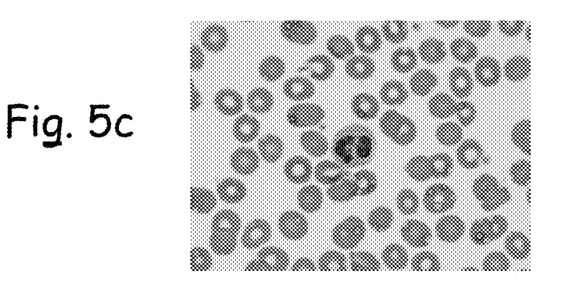
FIG. 5c shows a blood smear after a quick staining with a process that comprises a preliminary fixing stage for 5 minutes with ethanol at 99.9°+2% ethylene glycol+dimethyl sulfoxide+0 ml of water.
Figure 6A:
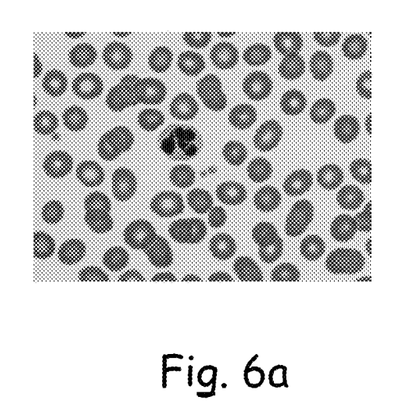
FIG. 6a shows a blood smear after a quick staining with a process that comprises a preliminary fixing stage for 5 minutes with ethanol at 99.9°+2% ethylene glycol+dimethyl sulfoxide+5 ml of water+0.1 g of sodium chloride.
Figure 6B:
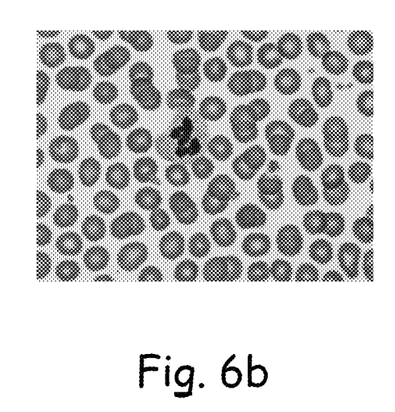
FIG. 6b shows a blood smear after a quick staining with a process that comprises a preliminary fixing stage for 5 minutes with ethanol at 99.9°+2% ethylene glycol+dimethyl sulfoxide+5 ml of water+0.3 g of sodium chloride.
Figure 6C:
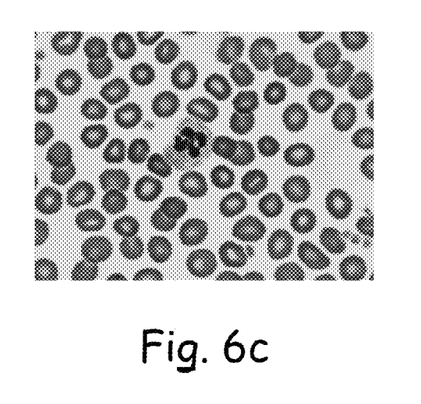
FIG. 6c shows a blood smear after a quick staining with a process that comprises a preliminary fixing stage for 5 minutes with ethanol at 99.9°+2% ethylene glycol+dimethyl sulfoxide+5 ml of water+0.2 g of sodium chloride.

According to another advantage, the invention makes it possible to obtain excellent visual contrasts, making possible a precise identification of different cellular types and, without a deposition of stain, a source of various artifacts. It is noted in particular in FIGS. 2a and 2b that the contrast that is obtained is better than the one that is obtained with the products of the prior art (FIGS. 1a, 1b, 1c, and 1d).

The invention is now illustrated by a non-limiting example that is applied to hematology.

EQUIPMENT

Fixing Composition (Product 1)

The fixing composition is prepared as disclosed below.
For 1 l of product:
A solution A is prepared by dissolving the following stains in 280 to 380 ml of DMSO: methylene blue-eosin, azure blue I-eosin, methylene blue, methylene azure blue I, and a compound of the group of thiazines,
A solution B is prepared by mixing between 550 and 680 ml of ethanol with approximately 1 ml of ethylene glycol,
A solution C is prepared by dissolving between 1 and 4 g of sodium chloride in 40 to 60 ml of water,
A solution D is prepared by adding the solution C, while being stirred, to the solution B,
The solution A is added to the solution D, while being stirred, and
The mixture is filtered.

Buffer (Product 2)

The buffer is prepared by the implementation of the operating procedure described below.
For 1 l of product, between 0.189 and 0.530 g of disodium phosphate, between 0.399 and 0.726 g of monopotassium phosphate, approximately 1 g of an anti-microbial agent, and approximately 1 g of a non-ionic surfactant are dissolved in approximately 1 l of water. The batch is then filtered.

Additional Staining Reagent (Product 3)

The additional staining reagent is prepared as follows.
For 1 l of product:
A first solution is prepared by dissolving the following stains into between 10 and 15 ml of DMSO: methylene blue, methylene azure blue I, and a compound from the group of thiazines,
A second solution is prepared by dissolving between 5 and 8 g of disodium phosphate and between 1.5 and 3 g of monopotassium phosphate into between 985 and 990 ml of water,
The first solution, while being stirred, is added to the second solution, and
The mixture is filtered.

Rinsing Liquid (Product 4)

For 1 l of product, the rinsing liquid is obtained by dissolving between 0.3 and 0.5 g of disodium phosphate, between 0.3 and 0.5 g of monopotassium phosphate, approximately 0.1 g of an anti-microbial agent, and between 45 and 50 g of alcohol (preferably isopropanol) in approximately 940 ml of water. The batch is then filtered.

Staining Process Example: Results of the "May-Grünwald Giemsa Staining" Type

To obtain results recognized by the specialists of the profession as a "May-Grünwald-Giemsa-staining"-type staining, it is possible to implement the series of following stages:
Bringing a plate that bears a blood or medullary smear to be analyzed into contact with the product 1 for 5 to 8 minutes,
Bringing the plate into contact with the product 2 for 2 to 3 minutes,
Bringing the plate into contact with the product 3 for 1 to 3 minutes, and
Bringing the plate into contact with the product 4 for 5 to 20 seconds, optionally by stirring gently.
After air-drying, the plates are ready to be observed directly under a microscope or by an image analysis system.
The results that are obtained are presented in FIG. 2a.

Staining Process Example: Results of the "Wright/Leishman Staining" Type

To obtain results recognized by the specialists of the profession as a "Wright/Leishman-staining"-type staining, it is possible to implement the series of the following stages:
Bringing a plate bearing a blood or medullary smear to be analyzed into contact with the product 1 for 5 to 10 minutes,
Bringing the plate into contact with the product 2 for 3 to 8 minutes, and
Bringing the plate into contact with the product 4 for 5 to 20 seconds, optionally by stirring gently.
After air-drying, the plates are ready to be observed directly under a microscope or by an image analysis system.
The results that are obtained are presented in FIG. 2b.

Of course, the invention obviously is not limited to the embodiment shown and described above, but on the contrary covers all of the variants.

The invention claimed is:
1. A composition for fixing tissues, and/or cells and/or cellular structures for the purpose of the staining and analysis thereof under a microscope or by an image analysis system, consisting of, with the percentages being provided by mass relative to the total composition:
between 40 and 60% ethanol or isopropanol,
between 30 and 40% dimethyl sulfoxide,
between 0.1 and 1% ethylene glycol,
between 2 and 12% water,
between 0.1 and 0.5% sodium chloride, and
at least one blue stain and at least one red stain,
wherein said composition does not contain methanol, picric acid, formaldehyde, glutaraldehyde, or osmic acid.
2. The composition of claim 1, wherein the at least one blue stain is selected from the group consisting of methylene blue, azure blue I, a blue stain that belongs to the group of thiazines, and combinations thereof, and wherein the at least one red stain is eosin and/or erythrosine.
3. A method for simultaneously carrying out fixing and staining of tissues and/or cells and/or cellular structures, comprising fixing and staining said tissues and/or cells and/or cellular structures on plates using a composition of claim 1.

4. A process of manufacturing a composition of claim 1, comprising the steps of:
- preparing a solution 4 of dimethyl sulfoxide, at least one blue stain, and at least one red stain;
- mixing either ethanol or isopropanol with ethylene glycol to obtain a solution 1;
- dissolving sodium chloride in water to obtain a solution 2;
- adding the solution 2 into the solution 1, while stirring, to obtain a solution 3;
- adding the solution 3, while stirring, into the solution 4 to form a mixture; and
- filtering the mixture.

5. The process of manufacturing according to claim 4, wherein the solution 4 is obtained by dissolving in dimethyl sulfoxide:
- methylene blue-eosin,
- azure blue I-eosin,
- methylene blue,
- methylene azure blue I, and
- a compound of the group of thiazines.

6. A method for staining a preparation of cells or cellular structure comprising bring the preparation to be stained into contact with a fixing composition of claim 1.

7. The method according to claim 6, wherein the preparation is blood or marrow.

8. A method for staining a preparation of cells or cellular structures, comprising the steps of: bringing the preparation to be stained into contact with a fixing composition of claim 1 to obtain a fixed preparation; bringing the fixed preparation into contact with a buffer solution at a pH of between 6.5 and 7.0; and bringing the fixed preparation into contact with a rinsing solution after contact with the buffer solution.

9. The method according to claim 8, wherein the preparation is blood or marrow.

10. A method for staining a preparation of cells or cellular structures comprising the steps of: bringing the preparation to be stained into contact with the fixing composition of claim 1 for 5 to 10 minutes to obtain a fixed preparation; bringing the fixed preparation into contact with a buffer solution at a pH of between 6.5 and 7.0 for 3 to 8 minutes; and bringing the fixed preparation into contact with a rinsing solution for 5 to 20 seconds after contact with the buffer solution.

11. The method according to claim 10, wherein the preparation is blood or marrow.

12. A method for staining a preparation of tissues and/or cells and/or cellular elements, comprising the steps of: bringing the preparation to be stained into contact with the fixing composition of claim 1 to obtain a fixed preparation; bringing the fixed preparation into contact with a buffer solution at a pH of between 6.8 and 7.2; bringing the fixed preparation into contact with an additional staining reagent after contact with the buffer solution; and bringing the fixed preparation contacted with an additional staining reagent into contact with a rinsing solution.

13. The method according to claim 12, wherein the preparation is blood or marrow.

14. A method for staining a preparation of tissues and/or cells and/or cellular elements, comprising the steps of: bringing the preparation to be stained into contact with the fixing composition of claim 1 for 5 to 8 minutes to obtain a fixed preparation; bringing the fixed preparation into contact with a buffer solution at a pH of between 6.8 and 7.2 for 2 to 3 minutes; bringing the fixed preparation into contact with an additional staining reagent for 1 to 3 minutes after contact with the buffer solution; and bringing the fixed preparation into contact with a rinsing solution for 5 to 20 seconds after contact with the additional staining reagent.

15. The method according to claim 14, wherein the preparation is blood or marrow.

* * * * *